United States Patent
Roh et al.

[11] Patent Number: 6,031,128
[45] Date of Patent: Feb. 29, 2000

[54] PROCESS FOR MANUFACTURING TEREPHTHALIC ACID

[75] Inventors: Hang-Duk Roh, Kyungki-do; Dongmok Bae, Seoul, both of Rep. of Korea

[73] Assignee: Sunkyong Industries Co., Ltd., Rep. of Korea

[21] Appl. No.: 09/101,008

[22] PCT Filed: Dec. 30, 1995

[86] PCT No.: PCT/KR95/00187

§ 371 Date: Jun. 29, 1998

§ 102(e) Date: Jun. 29, 1998

[87] PCT Pub. No.: WO97/24312

PCT Pub. Date: Jul. 10, 1997

[51] Int. Cl.[7] .......................... C07C 51/09; C07C 51/42; B09B 5/00

[52] U.S. Cl. .................. 562/483; 562/486; 422/184.1

[58] Field of Search .................. 562/483, 486; 422/184.1

[56] References Cited

U.S. PATENT DOCUMENTS

| | | | |
|---|---|---|---|
| 3,120,561 | 2/1964 | Chambret | 260/515 |
| 3,544,622 | 12/1970 | England | 260/515 |
| 3,884,850 | 5/1975 | Ostrowski | 260/2.3 |
| 3,952,053 | 4/1976 | Brown, Jr. et al. | 260/525 |
| 4,355,175 | 10/1982 | Pusztaszeri | 562/483 |
| 4,578,502 | 3/1986 | Cudmore | 560/790 |
| 5,210,292 | 5/1993 | Park et al. | 562/487 |
| 5,395,858 | 3/1995 | Schwartz et al. | 521/48 |

FOREIGN PATENT DOCUMENTS

| | | |
|---|---|---|
| 497662 | 1/1992 | European Pat. Off. . |
| 597751 | 10/1993 | European Pat. Off. . |
| 2508819 | 2/1975 | Germany . |
| 2123403 | 2/1984 | United Kingdom . |

OTHER PUBLICATIONS

Japanese Patent Unexamined Publication No. 50–104,276, dated Aug. 18, 1975.
Japanese Patent Unexamined Publication No. 61–43139, dated Mar. 1, 1986.
Japanese Patent Unexamined Publication No. 60–233033, dated Nov. 19, 1985.
Japanese Patent Unexamined Publication No. 60–216884, dated Oct. 30, 1985.
Japanese Patent Unexamined Publication No. 61–43140, dated Mar. 1986.
Japanese Patent Unexamined Publication No. 60–163843, dated Aug. 26, 1985.
Japanese Patent Unexamined Publication No. 60–19784, dated Jan. 31, 1985.

*Primary Examiner*—Porfirio Nazario-Gonzalez
*Attorney, Agent, or Firm*—Finnegan, Henderson, Farabow, Garrett & Dunner, L.L.P.

[57] ABSTRACT

This invention relates to a process for manufacturing terephthalic acid and more particularly, to a process of manufacturing and recovering the highly purified terephthalic acid using an alkali weight-reduction waste water discharged from weight-reduction process in a polyester textile dyeing complex, in accordance with the practice of this invention comprising the following procedures: polyethylene terephthalate (hereinafter referred to "PET") waste scrap materials are hydrolyzed to prepare the slurry of disodium terephthalate. Then, said slurry dissolved in water is adsorbed to remove impurities, and followed by acid-neutralization to obtain terephthalic acid of this invention.

16 Claims, 1 Drawing Sheet

PROCESS FOR MANUFACTURING TEREPHTHALIC ACID

CROSS-REFERENCE TO RELATED APPLICATIONS

This application is the national phase entry, under 35 U.S.C. § 371, of International Application No. PCT/KR95/00187, filed Dec. 30, 1995.

BACKGROUND OF THE INVENTION

Field of the Invention

This invention relates to a process for manufacturing terephthalic acid and more particularly, to a process of manufacturing and recovering the highly purified terephthalic acid using an alkali weight-reduction waste water discharged from weight-reduction process in a polyester textile dyeing complex, in accordance with the practice of this invention comprising the following procedures: polyethylene terephthalate (hereinafter referred to "PET") waste scrap materials are hydrolyzed to prepare the slurry of disodium terephthalate. Then, said slurry dissolved in water is adsorbed to remove impurities, and followed by acid-neutralization to obtain terephthalic add of this invention.

"Alkali weight-reduction waste water" is a remaining reactant discharged in a weight reduction-processing stage which is designed to give the polyester textile a silky property, as well as to improve the dyeing capability by treating the polyester textile with sodium hydroxide or another basic aqueous solution, and thereby causing a part of the textile to become depolymerization. Said alkali waste water is a strong alkali solution of over pH 11 with a large amount of sodium hydroxide and disodium terephthalate.

In the past, a considerable amount of alkali weight-reduction waste water, generated from the large industrial complex crowded with dyeing plants, has been directly discharged by a conventional waste water treatment. Besides that, sludges neutralized with such strong acid as hydrochloric acid or sulfuric acid have been used for landfills or sea-abandonments, while the remaining reactants have been discharged by a conventional waste water treatment. Therefore, alkali weight-reduction waste water generated from the conventional weight-reduction process for polyester textile has caused severe environmental problems and such treatment conventionally requires a large amount of investment for anti-pollution facilities.

In addition, the PET waste scrap materials, which are discharged after using them from the end-users, refer to polyester scrap textiles, PET scrap bottles, PET scrap containers, PET scrap chips generated in the polymerization process of PET, or polyester scrap yarns generated from the process of manufacturing polyester fibers, yarns and textiles. The need for the reutilization of the PET scrap, being incessantly discharged by one's daily life or in the manufacturing process, has created a great issue in the viewpoint of reducing production costs and abating environmental problems. Recently, various processes have been proposed for the recovery of terephthalic acid from the PET scrap, or polyester weight-reduction waste water but no process to manufacture and recover terephthalic acid, using both PET scrap and polyester weight-reduction waste water, has been reported up to now.

The conventional processes of manufacturing and recovering terephthalic acid are as follows, using the PET scrap:

In U.S. Pat. Nos. 3,120,561 and 4,578,502, PET was hydrolyzed at high temperature and pressure, cooled rapidly and crystallized to recover the precipitated terephthalic acid.

In U.S. Pat. No. 3,884,850, bis(hydroxyethyl) terephthalate was employed as a solvent to recover terephthalic acid from PET.

In U.K. Pat. No. 2,123,403 and Japanese Patent Unexamined Publication No. 3-16,328, PET was hydrolyzed with a solvent such as water in the presence of decoloring carbon at 200 to 300° C., then cooled under reduced pressure to recover terephthalic acid.

In U.S. Pat. No. 3,952,053, two methods related the recovery of terephthalic acid from PET as follows: a) through the hydrolysis with sulfuric acid, the obtained mixing solution consisting of terephthalic acid and sulfuric acid was precipitated by water to recover terephthalic acid, or b) PET was placed in an aqueous solution of sodium hydroxide to precipitate unsoluble materials for removal and sulfuric acid was added to precipitate terephthalic acid. Then, ethylene glycol was extracted with organic solvent and distilled after the recovery of terephthalic acid.

In U.S. Pat No. 4,355,175, PET was hydrolyzed by acid, diluted with cold water and filtered immediately. The resulting solution was dissolved in an aqueous solution of alkali hydroxide to precipitate impurities for removal and added with sulfuric acid to precipitate terephthalic acid. Then, the solution was filtered, washed with water and dried to recover terephthalic acid.

In U.S. Pat. No. 3,544,622, PET was reacted by saponification with an aqueous solution of sodium hydroxide at 150° C. in the presence of ethylene glycol, to prepare disodium terephthalate. Then, the resulting solution was filtered, washed with ethylene glycol or an aqueous solution of disodium terephthalate at over 90° C. and dissolved in water. Activated charcoal was added to the solution at 90° C., stirred and neutralized with sulfuric acid. Then, terephthalic acid was filtered and washed with water to recover terephthalic acid.

In European Patent No. 497,662, PET was reacted with alkali metal/earth metal hydroxide at atmospheric pressure and 140 to 180° C., to prepare terephthalic acid alkali metal/earth metal salt. This material was dissolved in water to extract impurities by alcohol having $C_3$ to $C_8$, then neutralized with acid and followed by filtration to recover terephthalic acid.

In European Patent No. 597,751, PET was reacted with sodium hydroxide in the presence of a mixing extruder without the addition of solvent and then, the obtained disodium terephthalate was dissolved in water, passed through activated charcoal and neutralized with sulfuric acid.

The resulting solution was filtered and washed to recover terephthalic acid.

In U.S. Pat. No. 5,395,858, PET dissolved in an aqueous solution of sodium hydroxide was heated to prepare both disodium terephthalate and ethylene glycol. These materials, so obtained, were heated up higher than boiling point of ethylene glycol to evaporate the solution. The remaining disodium terephthalate was dissolved in water and neutralized with acid to recover terephthalic acid.

The conventional processes of manufacturing and recovering terephthalic acid are as follows, using polyester weight-reduction waste water:

In Japanese Patent Unexamined Publication No. 50-104,276, terephthalic acid alkali salt was neutralized with sulfuric acid to give terephthalic acid.

In Japanese Patent Unexamined Publication No. 60-19,784, ultra-filtration was introduced to remove impurities and then, terephthalic acid was obtained through neutralization with sulfuric acid.

In Japanese Patent Unexamined Publication No. 60-163, 843, alkali waste water was centrifuged and neutralized with sulfuric acid to give terephthalic acid.

In Japanese Patent Unexamined Publication No. 60-216, 884, alkali waste water was passed through ion-exchange membrane to give terephthalic acid In Japanese Patent Unexamined Publication No. 60-233, 033, alkali waste water was neutralized at 120° C. and 1.7 atm to give terephthalic acid.

In Japanese Patent Unexamined Publication No. 61-43, 139, alkali waste water with low concentration was adjusted to pH 5 to 6 and pH 4 two times to deposit terephthalic acid and then, centrifuged to recover terephthalic acid.

In Japanese Patent Unexamined Publication No. 61-43, 140, hydrochloric acid was added to alkali waste water until the pH of the solution became 5.4 and treated with activated charcoal. Then, the solution was again added with hydrochloric acid until the pH of the solution became 2, and terephthalic acid was obtained.

In German Patent No. 2,508,819, alkali waste water was treated with sulfuric acid at 60 to 94° C. to give terephthalic acid;

In U.S. Pat. No. 5,210,292, alkali waste water was adjusted to pH 6 to 9, cooled to remove sodium sulfate and then, this material was again adjusted with sulfuric acid to pH 2 to 4 to give terephthalic acid.

These reported methods as aforementioned have also several problems as follows: a) a majority of their reactions was conducted at high temperature and pressure, b) they failed to illustrate some methods of removing impurities and monitoring purity, and c) the purity of terephthalic acid was not analyzed by appropriate methods for the quality measurements. In addition, in a process of filtering terephthalic acid as a final recovery step, the particle size of terephthalic acid should be sufficiently enlarged because small particles of terephthalic acid cause insufficient separation into solids and liquids which is responsible for reduction of recovery rate, and also make it difficult to perform the drying process. Nevertheless, said reported methods did not mention any steps of enlarging the particle sizes of terephthalic acid. In this context, said reported methods are technically and economically unfavorable for commercialization and further, there are still plenty of rooms for improving environmental problems, since said reported methods failed to suggest the method of treating by-products generated in the recovery process.

BRIEF DESCRIPTION OF THE DRAWINGS

The drawing is a schematic diagram showing the process of manufacturing terephthalic acid in accordance with this invention.

SUMMARY OF THE INVENTION

Figure 1:
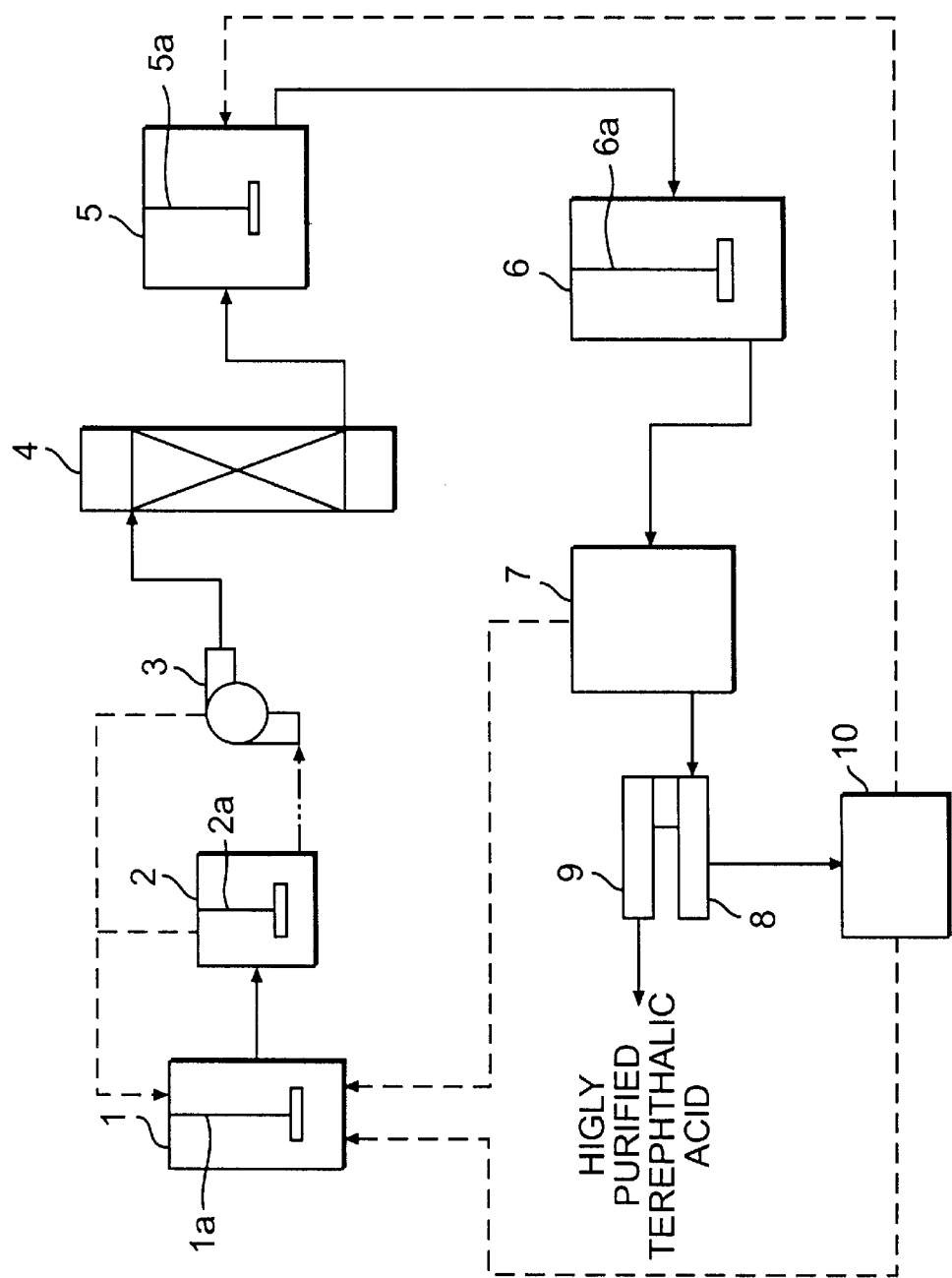

Therefore, the object of present invention is to provide a novel process for manufacturing terephthalic acid in accordance with the practice of this invention: a) Now that both PET scrap and alkali weight-reduction waste water, designed to manufacture terephthalic acid, are employed, said alkali weight-reduction waste water contains not only sodium hydroxide to be very useful in hydrolyzing the PET, but also disodium terephthalate to additionally recover terephthalic acid, which is economically feasible, and b) the solvents and reaction substances discharged during the reaction process was fed back for reuse, thus reducing the production costs of terephthalic acid.

DETAILED DESCRIPTION OF THIS INVENTION

The present invention may be described in more detail as shown below.

The present invention is characterized by a process for manufacturing and recovering terephthalic acid from the hydrolysis and crystallization processes of PET scrap comprising the following steps:

(a) a process in which PET scrap is hydrolyzed with both alkali weight-reduction waste water and a wetting agent, to prepare disodium terephthalate;

(b) a process in which an aqueous solution of disodium terephthalate dissolved in water is separated as solids and liquids; the solids are fed back to said (a) hydrolysis process or discharged, while the liquids are transferred to the next adsorption process;

(c) a process in which an aqueous solution of disodium terephthalate is adsorbed and neutralized with acid to give terephthalic acid;

(d) a crystallization process to enlarge the particle size of terephthalic acid;

(e) and, a process in which the enlarged particle of terephthalic acid is cooled under reduced pressure, filtered and dried.

The present invention also relates to several kinds of successively installed tanks for manufacturing terephthalic acid from PET scrap, which is characterized by the following systems: hydrolysis system (1) where said PET scrap is hydrolyzed with alkali weight-reduction waste water; dissolving system (2) where disodium terephthalate is dissolved; centrifuge (3); adsorption tower (4); neutralization system (5) where disodium terephthalate is neutralized with acid to prepare terephthalic acid; crystallization system (6) where the particle of terephthalic acid is enlarged; cooling system (7); filtering system (8) where the enlarged particle of terephthalic acid is filtered; drying system (9) where the filtered terephthalic acid is dried.

The present invention is described in more detail as set forth hereunder.

According to the present invention, a considerable amount of PET scrap discharged was hydrolyzed together with alkali weight-reduction waste water to prepare the slurry of disodium terephthalate. Then, the resulting solution is dissolved in water and impurities are removed during adsorption. The solution is neutralized with acid to prepare and recover terephthalic acid. In accordance with the practice of this invention, the highly purified terephthalic acid may be obtained in an easier manner. In addition, since the solvents and raw materials discharged in the reaction may be fed back, one can expect the reduction of production costs as well as to abate the environmental problems. The process of manufacturing terephthalic acid according to this invention is referred in more detail to the drawings as follows:

PET scrap (1 to 25 weight %), sodium hydroxide (1 to 30 weight %), alkali weight-reduction waste water (40 to 49%) and wetting agent (1 to 30 weight %) are charged into reaction tank (1), then stirred by agitator (1a), at pressure of 1 to 20 kg/cm$^2$ and temperature of 30 to 200° C. to proceed with hydrolysis reaction at 60 to 300 rpm for 30 to 120 mins.

During said hydrolysis reaction, in order to enlarge the reaction surface area of PET scrap, PET scrap is cut into small particles and pulverized in less than 1 cm$^3$ and then, charged into a reaction tank (1). Hence, if less than 1 weight % of charged PET scrap in reaction tank (1) is contained in a total volume of hydrolysis, there is no economic feasibility and in case of exceeding 25 weight %, a higher concentration of terephthalate salt makes it more difficult to operate the reaction in an efficient manner. And alkali weight-reduction waste material used in this invention refers to alkali waste material generated from the polyester textile weight-reduction process.

The composition of alkali weight-reduction waste water may differ based upon the weight-reduction ratio and washing rate, or upon the type of weight-reduction process (e.g., batch operation and continuous operation). In general, alkali weight-reduction waste water (specific gravity: 1.0 to 1.35, pH: 11 to 14) discharged from the polyester weight-reduction process contains sodium hydroxide of 1 to 25%, disodium terephthalate of 1 to 20%, ethylene glycol, additives used in the manufacture of polyester textile, excess water and other impurities. Therefore, the amount of alkali weight-reduction waste water may be changed in accordance with the content of sodium hydroxide contained in the alkali weight-reduction waste water and in addition, a mixture of alkali weight-reduction waste water and sodium hydroxide may be employed altogether. From said hydrolysis reaction, the concentration of sodium hydroxide contained in the amount of alkali weight-reduction waste water is 5 to 30 weight % in proportion to a total volume of reactants; If less than 5 weight % of sodium hydroxide is contained in the total volume of reactants, the conversion yield in reaction is low and in case of exceeding 30 weight %, there is no economic feasibility due to increased production cost and plenty of by-products to be inevitably generated. And according to this invention, a wetting agent may be selected from the group containing alcohols of $C_1$ to $C_4$ and surfactant.

If less than 1 weight % of said wetting agent is contained in a total volume of reactants, the reaction rate become low and in case of exceeding 30 weight %, the relative decrease of water content may enhance the concentration of disodium terephthalate and thus, the increased viscosity makes it difficult to operate the reaction in an efficient manner. In addition, if the reaction temperature in said hydrolysis is less than 30° C. or pressure is less than 1 kg/cm$^2$, the reaction rate becomes very low and there is no economic feasibility. In contrast, if the temperature in said hydrolysis reaction exceeds 200° C. or pressure also exceed 20 kg/cm$^2$, further hike in facility investment costs to maintain high reaction temperature/pressure and energy cost thereto will also make the process economically infeasible.

After said hydrolysis reaction, PET was converted to disodium terephthalate. Since the solubility of disodium terephthalate to water is about 13 weight % at room temperature, it may exist in the form of slurry.

The solution of disodium terephthalate is transferred from reaction tank (1) to dissolving tank (2). Said solution is added with water and stirred constantly by agitator (2a) at 60 to 300 rpm for 10 to 60 mins, at atmospheric pressure and 20 to 100° C. to dissolve disodium terephthalate in water. Hence, water in proportion to an aqueous solution of disodium terephthalate from said reactor is used in 0.5 to 3.0 times weight. If water is used in less than 0.5 times in weight, disodium terephthalate is not freely soluble in water and even if freely soluble, the viscosity of said solution is high so that the next adsorption process may not be operated in an efficient manner, while in the case of exceeding 3.0 times in weight, the size of both dissolving tank and adsorption tower is large in parallel with the gradual increase of water in use. Thus, additional facility investment cost and operation cost for reaction thereto should be inevitable.

The reaction in dissolving tank (2) is preferably be conducted at atmospheric pressure and temperature of 20 to 100° C. and in order to ensure better adsorption efficiency in the next adsorption process, the reaction condition exceeding 100° C. is not preferable. In addition, the evaporated alcohol and water in the solubility process is condensed and fed back to reaction tank (1).

An aqueous solution of disodium terephthalate, passed through dissolving tank (2), is also (3) separated solids and liquids by under centrifuge; the solids containing non-reactants and insoluble substances are fed back to reaction tank (1) or discharged, while the liquids are delivered to adsorption tower (4).

Adsorption tower (4) plays a role of removing impurities contained in PET (e.g., metal, metal compound, organic compound, dirt, etc.). The purity of terephthalic acid, a final product, is determined based upon the removal efficiency in adsorption tower (4). According to this invention, activated carbon as a filling material of adsorption tower (4), which is stable in alkali solution, is selected for use and in consideration of its adsorption rate, the surface area of activated carbon per unit volume is preferably 500 to 1,500 m$^2$/g. The reaction of adsorption tower (4) is preferably conducted at pressure of 0.01 to 10.0 kg/cm$^2$ and temperature of 20 to 100° C., so as to further enhance the efficiency of removing impurities.

The appropriate retention time in adsorption tower (4) is 1 to 60 mins but said retention time may be more or less adjusted in accordance with the reaction pressure.

An aqueous solution of disodium terephthalate, passed through adsorption tower (4), is transferred to neutralization tank (5) for neutralization with acid. While agitating by agitator (5a) in neutralization tank (5), said solution was mixed slowly with such strong acids as hydrochloric acid, sulfuric acid, nitric acid, phosphoric acid. Then, disodium terephthalate is neutralized to prepare terephthalic acid and sodium salt. During the neutralization reaction individually, two equivalence points are formed; the 1st equivalence point is detected when the pH of said solution becomes between 9.0 and 6.0, where the sodium hydroxide is neutralized with acid to prepare sodium salt, and the 2nd equivalence point is detected when the pH of said solution becomes between 4.0 and 2.0, where the disodium terephthalate is neutralized with acid to prepare terephthalic acid. During said neutralization reaction, therefore, acid should be incessantly provided until the pH of said solution becomes 4.0 to 2.0.

After said neutralization reaction, the obtained sodium salt is freely soluble in water due to its larger solubility to water, while terephthalic acid in wet cake is crystallized. Since the particle size of crystallized terephthalic acid is so small, terephthalic acid may not be efficiently separated by a method of separating solids and liquids (e.g., centrifugation or filtration). Even if separated, its recovery rate is quite low and thus, the commercial application is not economically feasible. According to this invention, therefore, the slurry of terephthalic acid, so obtained from said neutralization process, is charged into crystallization tank (6) to sufficiently enlarge the particle size of terephthalic acid.

One to five tanks in crystallization tank (6) is/are connected in series and each of crystallization tank (6) is fabricated in such a manner that temperature may be lowered stepwise. With said structure, the particle may be enlarged stepwise, thus making it possible to decrease the microparticles.

Crystallization temperature drop is preferably 30 to 50° C. and the total retention time required to completely pass through each of crystallization tank (6) is preferably 20 to 60 mins. In line with said process to enlarge the particle size of terephthalic acid, crystallization tank (6) should be operatable with the following specification: temperature in 120 to 300° C., pressure in 2 to 86 kg/cm$^2$ and agitation rate at 60 to 300 rpm. In addition, since the process of terephthalic acid crystallization is conducted at high temperature and pressure, excess acid may cause corrosion of crystallization tank (6).

In this connection, any acid contained in the slurry of terephthalic acid, passed through said neutralization process, should be lower than 10 weight %. Strong corrosion-resistant material should be selected such as stainless steel type 316 or titanium for crystallization tank.

The sufficiently enlarged terephthalic acid in said crystallization tank (6) is charged into the next cooling tank (7) and cooled at pressure of 0.1 to 1.0 kg/cm$^2$ and temperature of 60 to 90° C. under reduced pressure. Hence, alcohol contained in slurry is evaporated with water. The evaporated alcohol and water are condensed and then, fed back to reaction tank (1).

The slurry of cooled terephthalic acid is delivered to filter (8) to separate solids from liquids. The operating temperature of filter (8) depends on the slurry temperature of terephthalic acid and the temperature is preferably maintained at 60 to 80° C. The pressure is preferably 0.1 to 0.8 kg/cm$^2$. Based upon said method of separating solids and liquids, terephthalic acid is separated as wet cake, and sodium salt as liquid state together with water. The filtered terephthalic acid is washed with water and in consideration of washing efficiency, 0.5 to 1.2 times of water of terephthalic acid (30 to 80° C.) in proportion to terephthalic acid is preferably used.

The filtered terephthalic acid is charged into dryer (9) and dried at temperature of 100 to 150° C. and pressure of 0.5 to 1.0 kg/cm$^2$ for 10 to 120 mins, to give terephthalic acid, a final product of this invention.

In addition, the filtrate discharged from said filtration process is concentrated by the evaporation of water, or without evaporation of water, the filtrate is directly charged into electrodialyzer (10) using bipolar membrane, to individually separate acid and base of sodium hydroxide. Each of acid and base, so separated and recovered, is fed back to neutralization tank (5) and reaction tank (1), respectively. In a more detailed manner, acidic metal/earth metal salt (e.g., sodium hydrochloride or sodium sulfate) contained in said filtrate is electrolyzed. Na$^+$ ion, passed through cation membrane, is bound with OH$^-$ ion, to form sodium hydroxide.

In addition, the acidic anion such as Cl$^-$ ion or SO$_4^{2-}$ ion, passed through anion membrane, is bound with H$^+$ ion, to form such acids as hydrochloric acid or sulfuric acid.

As described in the above, this invention is intended to provide a process for reusing the feed-back reacting raw materials including solvents discharged from each of manufacturing step, thus making it possible to reduce production costs and also to abate environmental problems due to waste scrap materials.

Further, terephthalic acid, so separated and recovered from said manufacturing process, may be obtained with a high yield of 98% or better. This invention is explained in more detail by the following examples, but the claims are not limited to these examples.

EXAMPLE 1

550 ml of alkali weight-reduction waste water, 200 g of methanol and 10 g of pulverized PET were charged into reaction tank (1), and the mixture was stirred by agitator (300 rpm) at pressure of 8 kg/cm$^2$ and temperature of 150° C. for 120 mins.

The reacting solution in reaction tank (1) was transferred to dissolving tank (2), added with 400 g of water and stirred by agitator (2a, 60 rpm) at atmospheric pressure and temperature of 65° C. for 10 mins. Hence, the evaporated alcohol and water were condensed to feed back to reactor (1).

An aqueous solution of disodium terephthalate, passed through dissolving tank (2), was under centrifuge (3) to individually separate solids and liquids. The solids were fed back to reaction tank (1). 0.18 g of unreacting PET was contained in said solids and thus, it is well understood that the reaction rate of PET was 98.2%.

The liquids, passed through centrifuge (3), were transferred to adsorption tower (4) and adsorbed at pressure of 0.01 kg/cm$^2$ and temperature of 30° C. for 1 min. The adsorption tower (4) was filled with activated charcoal of surface area of 1,500 m$^2$/g.

An aqueous solution of disodium terephthalate, passed through adsorption tower (4), was transferred to neutralization tank (5). Then, the solution was stirred by agitator (5a) in neutralization tank and added slowly with hydrochloric acid and incessantly until the pH of solution became 4.0. As a result of monitoring by SEM, the particle size of terephthalic acid formed from said neutralization process, its particle size (10 to 15 μm) was very small.

In this connection, said neutralization solution was charged into crystallization tank (6) to enlarge the particle size of terephthalic acid. The crystallization tank (6) is of stainless steel type 316 or titanium and has the following requirements: temperature in 150° C., pressure in 5 kg/cm$^2$ and agitation rate at 60 rpm.

The sufficiently enlarged slurry of terephthalic acid in said crystallization tank (6) was charged into the next cooling tank (7) and cooled under reduced pressure, at pressure of 1 kg/cm$^2$ and temperature of 90° C. Hence, the evaporated methanol and water were condensed and fed back to reaction tank (1). The slurry of cooled terephthalic acid was delivered to filter (8) to individually separate solids and liquids, at pressure of 0.8 kg/cm$^2$ and temperature of 80° C. Then, terephthalic acid in wet cake was recovered. The filtered terephthalic acid was charged into dryer (9) and dried at pressure of 1 kg/cm$^2$ and temperature of 150° C. for 10 mins to give 18.9 g of terephthalic acid.

Further, the filtrate discharged from said filter (8) was charged into electrodialyzer (10) with 3 chamber-type bipolar membrane, and disodium hydrochloride contained in said filtrate was electrolyzed to separate hydrochloric acid and sodium hydroxide. Then, each of them was individually fed back to reaction tank (1) or neutralization tank (5).

EXAMPLE 2

455 g of alkali weight-reduction waste water, 135 g of sodium hydroxide, 300 g of methanol, 1 g of surfactant (SURMAX CS 727, Chemax Inc.) and 150 g of pulverized PET were charged into reaction tank (1), and the mixture was stirred by an agitator (100 rpm) at pressure of 5 kg/cm$^2$ and temperature of 100° C. for 120 mins.

The solution in reaction tank (1) was transferred to dissolving tank (2), added with 1,000 g of water and stirred by agitator (2a, 300 rpm) at atmospheric pressure and temperature of 80° C. for 60 mins. Hence, the evaporated alcohol and water were condensed to feed back to reactor (1).

An aqueous solution of disodium terephthalate, passed through dissolving tank (2), was under centrifuge (3) to individually separate solids and liquids. The solids were fed back to reaction tank (1). 16 g of unreacting PET was contained in said solids and thus, it is well understood that the reaction rate of PET was 89.3%.

The liquids, passed through centrifuge (3), were transferred to adsorption tower (4) and adsorbed at pressure of 0.1 kg/cm$^2$ and temperature of 90° C. for 60 mins. The adsorption tower (4) was filled with activated charcoal of surface area of 1,500 m$^2$/g.

An aqueous solution of disodium terephthalate, passed through adsorption tower (4), was transferred to neutralization tank (5). Then, the solution was stirred by agitator (5a) in neutralization tank and added slowly with 97% sulfuric acid and incessantly until the pH of solution became 4.0. As a result of monitoring by SEM, the particle size of terephthalic acid formed from said neutralization process, its particle size (10 to 20 μm) was very small.

In this connection, said neutralization solution was charged into crystallization tank (6) to enlarge the particle of terephthalic acid. The crystallization tank (6) is of stainless steel type 316 which was connected with two crystallization tanks in series and each of crystallization tank has the following requirements: temperature in 150° C., pressure in 5 kg/cm$^2$ and agitation rate at 300 rpm. The total retention time, passed through the whole crystallization tank (6), was 60 mins.

The sufficiently enlarged slurry of terephthalic acid in said crystallization tank (6) was charged into the next cooling tank (7) and cooled under reduced pressure, at pressure of 1 kg/cm$^2$ and temperature of 60° C. Hence, the evaporated methanol and water were condensed and fed back to reaction tank (1). The slurry of cooled terephthalic acid was delivered to filter (8) to individually separate solids and liquids, at pressure of 0.5 kg/cm$^2$ and temperature of 60° C. Then, terephthalic acid in wet cake was recovered.

The filtered terephthalic acid was charged into dryer (9) and dried at pressure of 1 kg/cm$^2$ and temperature of 100° C. for 60 mins to give 123 g of terephthalic acid.

Further, the filtrate discharged from said filter (8) was charged into electrodialyzer (10) with 3 chamber-type bipolar membrane and sodium sulfate contained in said filtrate was electrolyzed to separate sulfuric acid and sodium hydroxide. Then, each of them was individually fed back to reaction tank (1) or neutralization tank (5).

EXAMPLE 3

650 g of alkali weight-reduction waste water, 40 g of sodium hydroxide, 200 g of methanol and 110 g of pulverized PET were charged into reaction tank (1), and the mixture was stirred by agitator (100 rpm) at pressure of 20 kg/cm$^2$ and temperature of 200° C. for 60 mins.

The reacting solution in reaction tank (1) was transferred to dissolving tank (2), added with 2,500 g of water and stirred by agitator (2a, 200 rpm) at atmospheric pressure and temperature of 100° C. for 30 mins. Hence, the evaporated alcohol and water were condensed to feed back to reactor (1).

An aqueous solution of disodium terephthalate, passed through dissolving tank (2), was under centrifuge (3) to individually separate solids and liquids. The solids were fed back to reaction tank (1). 3.9 g of unreacting PET was contained in said solids and thus, it is well understood that the reaction rate of PET was 96.5%.

The liquids, passed through centrifuge (3), were transferred to adsorption tower (4) and adsorbed at pressure of 1 kg/cm$^2$ and temperature of 90° C. for 60 mins. The adsorption tower (4) was filled with active charcoal of surface area of 1,500 m$^2$/g.

An aqueous solution of disodium terephthalate, passed through adsorption tower (4), was transferred to neutralization tank (5). Then, the solution was stirred by agitator (5a) in neutralization tank and added slowly with 97% sulfuric acid and incessantly until the pH of solution became 4.0. As a result of monitoring by, SEM the particle size of terephthalic acid formed from said neutralization process, its particle size (10 to 20 μm) was very small.

In this connection, said neutralization solution was charged into crystallization tank (6) to enlarge the particle size of terephthalic acid. The crystallization tank (6) is of stainless steel type 316 or titanum connected with five crystallization tanks in series and each of crystallization tank has the following requirements: pressure in 86 kg/cm$^2$ and agitation rate at 100 to 200 rpm. In addition, the temperature of the first crystallization tank was determined at 300° C. in such a fabrication that the temperature of said crystallization tank was lowered to 30 to 50° C. and the total retention time, passed through the whole crystallization tank (6), was 180 mins.

The sufficiently enlarged slurry of terephthalic acid slurry in said crystallization tank (6) was charged into the next cooling tank (7) and cooled under reduced pressure, at pressure of 1 kg/cm$^2$ and temperature of 90° C. Hence, the evaporated methanol and water were condensed and fed back to reaction tank (1). The slurry of cooled terephthalic acid was delivered to filter (8) to individually separate solids and liquids, at pressure of 0.1 kg/cm$^2$ and temperature of 80° C. Then, terephthalic acid in wet cake was recovered. The filtered terephthalic acid was charged into dryer (9) and dried at pressure of 0.8 kg/cm$^2$ and temperature of 120° C. for 120 mins to give 99.6 g of terephthalic acid.

Further, the filtrate discharged from said filter (8) was charged into electrodialyzer (10) with 3 chamber-type bipolar membrane and sodium sulfate contained in said filtrate was electrolyzed to individually separate sulfuric acid and sodium hydroxide. Then, each of them was individually fed back to reaction tank (1) or neutralization tank (5).

EXPERIMENT

Each of terephthalic acid, so obtained from said EXAMPLE 1 to 3, was analyzed by the following methods:

(1) Purity: As for terephthalic acid, so obtained from PET, μ-bondapak C18 column was introduced to monitor the concentration of its impurities on high pressure liquid chromatography (HPLC).

(2) Average particle size: Sieve analysis method and SEM were introduced to monitor average particle size.

(3) Transmittance: With a solution prepared by dissolving terephthalic acid in an aqueous solution of potassium hydroxide, spectrometer SPECTRONIC 601(MILTON ROY) was introduced to monitor its transmittance at 340 nm.

(4) Color value: DIANO Match Scan II Colorimeter was introduced to monior the values of color L, a and b.

(5) Metal content: XRF (X-ray refractive fluorescence) was introduced to monitor the metal content of Co, Mn and Fe.

TABLE

|  | EXAMPLE | | | Comparison | |
| --- | --- | --- | --- | --- | --- |
|  | 1 | 2 | 3 | 1 | 2 |
| Recovery rate (%) | 96.9 | 98.4 | 93 | 93 | 78 |
| Purity (%) | 99.1 | 98.0 | 99.6 | 98 | 99 |
| Average particle size ($\mu$m) | 54 | 66 | 92 | — | — |
| Transmittance (%) | 59.8 | 70.1 | 91.4 | — | — |
| Color value | | | | | |
| L | 97.9 | 96.6 | 97.3 | — | — |
| a | −0.5 | −0.5 | −0.4 | — | — |
| b | 1.1 | 1.7 | 1.3 | — | — |
| Metal content (ppm) | | | | | |
| Co | 0 | 0 | 0.1 | — | — |
| Mn | 0 | 0 | 0 | — | — |
| Fe | 4.6 | 7.2 | 16.1 | — | — |

COMPARISON 1: U.S. Pat. No. 3,120,561
COMPARISON 2: U.S. Pat. No. 4,355,175

The results of said table show that the purity of terephthalic acid, so obtained EXAMPLE 1 to 2, was more or less low but this was owing to the fact that isophthalic acid was contained in the process of manufacturing PET. The terephthalic acid containing isophthalic acid is useful in preparing polyester resin.

Therefore, now that terephthalic acid recovered by the methods of this invention does not contain any metals and also maintain a high purity, it is very useful in preparing polyester resin.

In addition, now that said COMPARISON 1 and 2 failed to describe the method of analyzing the quality of terephthalic acid, it is impossible to compare the values obtained from the EXAMPLE.

What is claimed is:

1. A process for manufacturing terephthalic acid wherein polyethylene terephthalate is hydrolyzed and crystallized to give terephthalic acid, in accordance with the practice of this invention comprising the following procedures:

(a) a process in which PET scrap is hydrolyzed with alkali weight-reduction waste water and wetting agent, to prepare disodium terephthalate;

(b) a process in which an aqueous solution of disodium terephthalate dissolved in water is separated as solids and liquids; the solids are fed back to said (a) hydrolysis process or discharged, while the liquids are transferred to the next adsorption process;

(c) a process in which an aqueous solution of disodium terephthalate is adsorbed and neutralized with acid to give terephthalic acid;

(d) a crystallization process to enlarge the particle of terephthalic acid;

(e) and, a process in which the enlarged particle of terephthalic acid is cooled under reduced pressure, filtered and dried.

2. The process for manufacturing terephthalic acid as claimed in claim 1 wherein in (a) step, polyethylene terephthalate waste scrap materials may for use include polyester textiles scrap, polyethylene terephthalate scrap bottle, polyethylene terephthalate scrap container, polyethylene terephthalate scrap chip generated in the polymerization process of polyethylene terephthalate, or polyester scrap yarn generated from the process of manufacturing polyester fibers, yarns and textiles.

3. The process for manufacturing and recovering terephthalic acid as claimed in claim 1 or 2 wherein 1 to 25 weight % of said polyethylene terephthalate scrap is added in a total volume of hydrolysis.

4. The process for manufacturing terephthalic acid as claimed in claim 1 wherein in (a) step, alkali weight-reduction waste water uses the waste water discharged from the polyester textile weight-reduction process.

5. The process for manufacturing terephthalic acid as claimed in claim 4 wherein 5 to 30 weight % of sodium hydroxide from said alkali weight-reduction waste water is contained in a total volume of hydrolysis.

6. The process for manufacturing terephthalic acid as claimed in claim 5 wherein said alkali weight-reduction waste water contains 1 to 20% of sodium hydroxide.

7. The process for manufacturing terephthalic acid as claimed in claim 5 wherein said alkali weight-reduction waste water is added together with sodium hydroxide.

8. The process for manufacturing terephthalic acid as claimed in claim 1 wherein 1 to 30 weight % of said wetting agent is contained in a total volume of hydrolysis.

9. The process for manufacturing terephthalic acid as claimed in claim 1 wherein said (a) step is conducted at pressure of 1 to 20 kg/cm$^2$ and 30 to 200° C.

10. The process for manufacturing terephthalic acid as claimed in claim 1 wherein in (b) step, 0.5 to 3.0 times of water in weight is used in proportion to an aqueous solution of disodium terephthalate.

11. The process for manufacturing terephthalic acid as claimed in claim 1 wherein said (d) step is conducted in the crystallization tank where one to five crystallization tanks is/are connected in series and the temperature of each crystallization tank dros stepwise by 30 to 50° C.

12. The process for manufacturing terephthalic acid as claimed in claim 11 wherein said crystallization tank is kept constant at pressure of 2 to 86 kg/cm$^2$ and temperature of 120 to 300° C.

13. The process for manufacturing terephthalic acid as claimed in claim 1 wherein said (e) step is conducted at pressure of 0.1 to 1.0 kg/cm$^2$ and temperature of 60 to 90° C.

14. The process for manufacturing terephthalic acid as claimed in claim 1 or 13 wherein alcohol and water discharged from said (e) step are fed back to said (a) step.

15. The process for manufacturing terephthalic acid as claimed in claim 1 wherein the filtrate discharged from said (e) step is charged into an electrodialyzer using bipolar membrane, to separate acid and sodium hydroxide; then, acid is fed back to said (c) step and sodium hydroxide is fed back to said (a) step.

16. A successively installed system for manufacturing terephthalic acid from polyethylene terephthalate waste scrap materials wherein it comprises: hydrolysis system (1) where said PET scrap is hydrolyzed with alkali weight-reduction waste water; dissolving system (2) where disodium terephthalate is dissolved; centrifuge (3); adsorption tower (4); neutralization system (5) where disodium terephthalate is neutralized with acid to prepare terephthalic acid; crystallization system (6) where the particle of terephthalic acid is enlarged; cooling system (7); filtering system (8) where the enlarged particle of terephthalic acid is filtered; drying system (9) where the filtered terephthalic acid is dried.

* * * * *